United States Patent
Murakoso et al.

(10) Patent No.: US 11,529,294 B2
(45) Date of Patent: Dec. 20, 2022

(54) OIL-IN-WATER EMULSION COSMETIC

(71) Applicants: NIKKO CHEMICALS CO., LTD., Tokyo (JP); NIPPON SURFACTANT INDUSTRIES CO., LTD., Tokyo (JP); COSMOS TECHNICAL CENTER CO., LTD., Tokyo (JP)

(72) Inventors: Keiko Murakoso, Tokyo (JP); Sayaka Tanaka, Tokyo (JP)

(73) Assignees: Nikko Chemicals Co., Ltd., Tokyo (JP); Nippon Surfactant Industries Co., Ltd., Tokyo (JP); Cosmos Technical Center Co., Ltd., Tokyo (JP)

( * ) Notice: Subject to any disclaimer, the term of this patent is extended or adjusted under 35 U.S.C. 154(b) by 175 days.

(21) Appl. No.: 16/499,479

(22) PCT Filed: Apr. 4, 2017

(86) PCT No.: PCT/JP2017/014068
§ 371 (c)(1),
(2) Date: Sep. 30, 2019

(87) PCT Pub. No.: WO2018/179451
PCT Pub. Date: Oct. 4, 2018

(65) Prior Publication Data
US 2020/0030201 A1 Jan. 30, 2020

(30) Foreign Application Priority Data
Mar. 30, 2017 (JP) .............................. JP2017-067233

(51) Int. Cl.
*A61K 8/06* (2006.01)
*A61K 8/34* (2006.01)
*A61K 8/362* (2006.01)
*A61K 8/365* (2006.01)
*A61K 8/37* (2006.01)
*A61K 8/44* (2006.01)
*A61K 8/67* (2006.01)

(52) U.S. Cl.
CPC ............. *A61K 8/062* (2013.01); *A61K 8/34* (2013.01); *A61K 8/362* (2013.01); *A61K 8/365* (2013.01); *A61K 8/37* (2013.01); *A61K 8/44* (2013.01); *A61K 8/676* (2013.01)

(58) Field of Classification Search
CPC .................................................... A61Q 19/00
See application file for complete search history.

(56) References Cited

U.S. PATENT DOCUMENTS

| 5,855,893 | A | 1/1999 | Weinkauf et al. |
| 6,551,604 | B1 * | 4/2003 | Beck ...................... A61Q 19/08 514/277 |
| 8,926,996 | B2 * | 1/2015 | Yoshimura ............... A61K 8/39 424/401 |
| 2011/0229538 | A1 | 9/2011 | Matravers et al. |

FOREIGN PATENT DOCUMENTS

| CN | 1196237 A | 10/1998 |
| CN | 102905681 A | 1/2013 |
| EP | 0858799 A2 | 8/1998 |
| JP | 07232051 A | 9/1995 |
| JP | 09065864 A | 3/1997 |
| JP | 10226634 A | 8/1998 |
| JP | 3253735 B2 | 2/2002 |
| JP | 2003238380 A | 8/2003 |
| JP | 2003306419 A | 10/2003 |
| JP | 2003342159 A | 12/2003 |
| JP | 2004051566 A | 2/2004 |
| JP | 2004331524 A | 11/2004 |
| JP | 2004339133 A | 12/2004 |
| JP | 2004339133 A * | 12/2004 |
| JP | 2005336116 A | 12/2005 |
| JP | 2009269851 A | 11/2009 |
| JP | 2015078167 A | 4/2015 |

OTHER PUBLICATIONS

Tada, K., JP 2004339133 A, Dec. 2, 2004, Tables 1 and 2, partial translation. (Year: 2004).*
English language International Preliminary Report on Patentability with Written Opinion for PCT/JP2017/014068, dated Jun. 20, 2017 (8 pages).
Atsushi Fujita, Prediction of Organic Compounds by a Conceptional Diagram, Pharmaceutical Bulletin, Jan. 1, 1954, pp. 163-173.
Extended European Search Report and opinion for corresponding Application No. 17903380.8 dated Jul. 10, 2020 (7 pages).
English and Japanese language International Search Report for PCT/JP2017/014068, dated Jun. 20, 2017 (5 pages).
Japanese language Notification of Transmittal of the International Search Report and the Written Opinion for PCT/JP2017/014068, dated Jun. 20, 2017 (7 pages).

(Continued)

*Primary Examiner* — Gina C Justice
(74) *Attorney, Agent, or Firm* — Flynn Thiel, P.C.

(57) ABSTRACT

An oil-in-water emulsion cosmetic containing (A) to (E) as essential components and having a pH of 6 or less:
(A) an L-ascorbyl tetra fatty acid ester derivative represented by the following general formula (I)

Formula 1

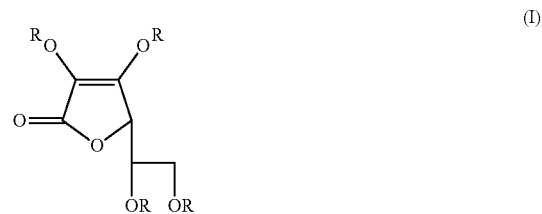

(I)

wherein R represents a branched alkyl fatty acid residue having 8 to 18 carbons;
(B) a polar oil which is liquid at 25° C. and having an IOB value of 0.1 to 0.5; (C) a chelating agent; (D) an antioxidant; and (E) water.

4 Claims, No Drawings

(56) References Cited

OTHER PUBLICATIONS

Cosmetics Handbook, edited by Nikko Chemicals Co., Ltd., published Nov. 1, 1996, pp. 395-398, with English translation of excerpt therefrom (5 pages).
Organic Conception Diagram—Fundamentals and Applications, by Yoshio Koda, published by Sankyo Shuppan Co., Ltd., 1984, pp. 11-17, with English translation of excerpts therefrom.
Office Action of European Patent Office issued in corresponding European Patent Application No. 17 903 380.8 dated May 11, 2022 (5 pages).
Chinese Office Action issued in corresponding Chinese Application No. 201780089144.0 dated Jan. 24, 2022 (7 pages).

\* cited by examiner

OIL-IN-WATER EMULSION COSMETIC

FIELD OF THE INVENTION

The present invention relates to an oil-in-water emulsion cosmetic having excellent stability of an L-ascorbyl tetra fatty acid ester derivative.

BACKGROUND OF THE INVENTION

The L-ascorbyl fatty acid ester has bioactive and pharmacological effects of vitamin C, and is lipophilic unlike L-ascorbic acid and L-ascorbate. Thus, it has been used particularly in cosmetics containing a large amount of oil phase components, for imparting vitamin C activity to the cosmetics (see, Cosmetics Handbook, p. 395-398, edited by Nikko Chemicals Co., Ltd., published on Nov. 1, 1996; JP-A 9-65864 and JP-A 7-232051).

However, the L-ascorbyl fatty acid ester has a melting point as high as 110° C. to 120° C. and low solubility in fat and oil and is not soluble in water. Accordingly, blending of the L-ascorbyl fatty acid ester is necessary for obtaining sufficient bioactive functions into a cosmetic requires the L-ascorbyl fatty acid ester to be added first into an oil phase component in a heated state of 80° C. or more, then to be mixed and dissolved.

To solve the above problems, JP-B 3253735 proposes inventions of a certain L-ascorbyl tetra fatty acid ester derivative and a cosmetic containing the same.

Further, JP-A 2003-238380, JP-A 2003-342159, JP-A 2003-306419, and JP-A 2004-51566 propose inventions of cosmetics containing the certain L-ascorbyl tetra fatty acid ester derivative described in JP-B 3253735.

To improve the stability of the L-ascorbyl tetra fatty acid ester in a preparation, a method for preventing coloration and generation of odor by using sulfurous acid, sulfite, bisulfite, hydrogensulfite, pyrosulfurous acid, and pyrosulfite (JP-A 2004-331524) has been reported, but the results were not sufficiently satisfactory.

SUMMARY OF THE INVENTION

Technical Problem

The present invention provides a cosmetic having increased stability over time obtained by inhibiting the hydrolysis of a certain L-ascorbyl tetra fatty acid ester derivative, which is the component contained in the cosmetic.

Solution to Problem

The present inventors have conducted intensive studies to improve stability of an L-ascorbyl tetra fatty acid ester derivative in an oil-in-water emulsion cosmetic, and as a result, found that an oil-in-water emulsion cosmetic containing the following (A) to (E) as essential components and having a pH of 6 or less inhibits the hydrolysis of the L-ascorbyl tetra fatty acid ester derivative and shows excellent stability, thereby completed the present invention:

(A) an L-ascorbyl tetra fatty acid ester derivative represented by the following general formula (I)

[Formula 1]

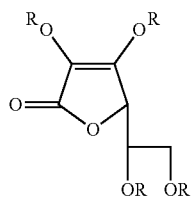

(I)

wherein R represents a branched alkyl fatty acid residue having 8 to 18 carbons;
(B) a polar oil which is liquid at 25° C. and having an IOB value of 0.1 to 0.5;
(C) a chelating agent;
(D) an antioxidant; and
(E) water.

Advantageous Effects of the Invention

The oil-in-water emulsion cosmetic of the present invention provides a cosmetic that is stable and can exert effects, such as melanogenesis inhibitory effect, melanin reducing effect, collagen production promoting effect, antioxidative effect, and lipid peroxide inhibitory effect for a long period of time, by inhibiting the hydrolysis of the L-ascorbyl tetra fatty acid ester derivative of component (A).

EMBODIMENTS OF THE INVENTION

Hereinafter, preferred embodiments according to the present invention will be described in detail.

The present invention is an oil-in-water emulsion cosmetic containing components (A) to (E) as essential components and having a pH of 6 or less.

<Component (A)>

Component (A) used in the present invention is an L-ascorbyl tetra fatty acid ester derivative represented by the following general formula (I).

[Formula 1]

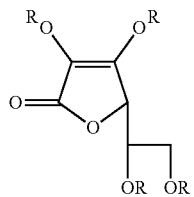

(I)

R represents a branched alkyl fatty acid residue having 8 to 18 carbons in general formula (I).

The L-ascorbyl tetra fatty acid ester represented by general formula (I) is not particularly limited, as long as R is the branched fatty acid having 8 to 18 carbons. Specifically, examples thereof include branched alkyl fatty acid residues having 8 to 18 carbons such as 2-ethylhexanoic acid, 3,5,5-trimethylhexanoic acid, isopalmitic acid, and isostearic acid. When R is a branched alkyl fatty acid residue, the ester can be conveniently handled, since it is liquid at room temperature.

The lower ester in which R has less than 8 carbons has poorer solubility in oil and the one in which R has more than 18 carbons has increased oily feeling and stickiness.

The L-ascorbyl tetra fatty acid ester represented by general formula (I) is the L-ascorbyl tetra fatty acid ester described in JP-B 3253735 and can be produced by the production method described therein. A commercial product, NIKKOL VC-IP (made by Nikko Chemicals Co., Ltd), is also available.

The content ratio of component (A) in the cosmetic is preferably 0.001 to 50.0% by mass, and more preferably 0.01 to 30.0% by mass. The preferred blending proportion varies in accordance with the form of the cosmetic.

<Component (B)>

Component (B) used in the present invention is a polar oil which is liquid at 25° C. and having an IOB value of 0.1 to 0.5. By containing component (B), the hydrolysis of component (A) in the cosmetic is inhibited.

The IOB value in the present invention is an abbreviation of "Inorganic/Organic Balance," and is a value corresponding to the ratio of the inorganic value of a compound to the organic value of the compound, which is an index of the polarity of an organic compound. Specifically, the IOB value is indicated as IOB value=inorganic value/organic value.

As for each "inorganic value" and "organic value," the "inorganic value" and "organic value" are determined for the individual atom or functional group, for example, an "organic value" of 20 for a carbon atom in a molecule and an "inorganic value" of 100 for a hydroxyl group in the molecule, and thus, the IOB value of an organic compound is calculated by adding "inorganic values" and "organic values" of all the atoms and functional groups in the organic compound (see, for example, "Organic Conception Diagram—Fundamentals and Applications—" written by Yoshio Koda, p. 11-17, published by Sankyo Shuppan Co., Ltd., 1984).

Examples of the polar oil used as component (B) include the followings:

cetyl ethylhexanoate (0.128), ethylhexyl palmitate (0.128), isopropyl myristate (0.182), macadamia nut oil (0.17), olive oil (0.16), isononyl isononanoate (0.2), caprylic/capric/stearic triglyceride (0.23), caprylic/capric triglyceride (0.274), diethylene glycol distearate (0.24), diethylene glycol diisostearate (0.25), diethylene glycol dioleate (0.25), neopentyl glycol dicaprate (0.25), propylene glycol dicaprate (0.26), dioctyldodecyl stearoyl glutamate (0.26), ethylhexyl methoxycinnamate (0.28), dioctyldodecyl lauroyl glutamate (0.29), triethylhexanoin (0.353), propylene glycol oleate (0.39), ethylene glycol dioctanoate (0.35), diethylene glycol dilaurate (0.35), glyceryl monostearate diacetate (0.36), trimethylolpropane trioctanoate (0.33), propylene glycol monostearate (0.38), octyldodecyl lactate (0.36), oleyl lactate (0.39), castor oil (0.42), propylene glycol isostearate (0.4), diethylene glycol dicaprate (0.41), propylene glycol dicaproate (0.4), diisopropyl sebacate (0.4), diethyl sebacate (0.43), ethylene glycol palmitate (0.44), methyl ricinoleate (0.43), ethylene glycol monooleate (0.41), ethylene glycol monostearate (0.4), and cetyl lactate (0.42).

Among them, ester oils such as cetyl ethylhexanoate, ethylhexyl palmitate, isopropyl myristate, caprylic/capric triglyceride, and triethylhexanoin; and vegetable oils such as olive oil, macadamia nut oil, castor oil are more preferable. Cetyl ethylhexanoate, ethylhexyl palmitate, caprylic/capric triglyceride, and triethylhexanoin are further preferable. The numerical values in parentheses represent reference IOB values.

The content ratio of component (B) in the cosmetic is preferably 10 to 100% by mass, and more preferably 40 to 100% by mass based on all the liquid oil except the L-ascorbyl tetra fatty acid ester.

<Component (C)>

Component (C) used in the present invention is a chelating agent. By containing component (C), the hydrolysis of component (A) in the cosmetic is inhibited. Examples of component (C) include one or two or more selected from edetic acid (EDTA) and a salt thereof, succinic acid and a salt thereof, and pentetic acid and a salt thereof. Among them, EDTA or succinic acid is preferable.

The content ratio of component (C) in the cosmetic is preferably 0.01 to 0.30% by mass, and more preferably 0.01 to 0.20% by mass.

<Component (D)>

Component (D) used in the present invention is an antioxidant. By containing component (D), the hydrolysis of component (A) in the cosmetic can be inhibited.

Examples of component (D) include ascorbic acid, tocopherol, glutathione, butylhydroxyanisole (BHA), dibutylhydroxytoluene (BHT), ascorbyl stearate, and ascorbyl palmitate. In order to blend in cosmetic products, tocopherol is preferred.

The content ratio of component (D) in the cosmetic is preferably 0.01 to 0.50% by mass, and more preferably 0.05 to 0.30% by mass.

<Component (E)>

The water used as component (E) preferably contains no alkali metal ions derived from alkali metals such as sodium and potassium, or preferably contains alkali metal ions as little as possible, and ion-exchange water, distilled water, filtered water obtained by reverse osmosis membrane and the like can be used from.

<Component (F)>

The cosmetic of the present invention may further contain a pH adjuster of component (F). The pH adjuster containing a buffer solution may also be used. Specifically, component (F) may contain one or two or more selected from citric acid and a salt thereof, succinic acid and a salt thereof, phosphoric acid and a salt thereof, sodium hydroxide, and potassium hydroxide.

The content ratio of component (F) in the cosmetic and the content ratio of the acid and alkali described above fall within a range in which the pH of the cosmetic of the present invention can be adjusted to a pre-determined value.

<Component (G)>

The cosmetic of the present invention can further contain a higher alcohol having 16 or more carbons of component (G) as an oily material or an emulsion stabilizer in the cosmetic.

By containing component (G), the hydrolysis of component (A) in the cosmetic can be inhibited as compared with the case of containing a higher alcohol having less than 16 carbons.

Examples of component (G) include cetyl alcohol, cetostearyl alcohol, stearyl alcohol, oleyl alcohol, and behenyl alcohol, and stearyl alcohol and behenyl alcohol having 18 or more carbons are preferable.

The content ratio of component (G) in the cosmetic is preferably 8% by mass or less, and more preferably 0 to 5% by mass. By containing 5% by mass or less of component (G), the hydrolysis of component (A) in the cosmetic can be inhibited.

<Other Components>

The cosmetic of the present invention may contain known components blended in cosmetic products, within a range not impairing the effects of the present invention.

Examples of the known components include a hydrocarbon such as a liquid paraffin, vegetable fat and oil, a wax, a moisturizing agent, a thickening agent, an ultraviolet absorber, a powder, a pigment, a coloring material, an anionic surfactant, a cationic surfactant, a nonionic surfactant, an amphoteric surfactant, a saccharide, a polymer compound, a bioactive component, a transdermal absorption promoting agent, a solvent, a perfume, and a preservative.

The cosmetic of the present invention has a pH of 6 or less, and preferably has a pH of 5.5 or less. When the pH of the cosmetic is 6 or less, the hydrolysis of component (A) in the cosmetic can be inhibited.

The cosmetic of the present invention consists of components (A) to (E), and additionally, component (G) and known components. When the cosmetic containing the respective components described above has a pH of 6 or less, the pH adjuster of component (F) is not required, and when the cosmetic has a pH of more than 6, the pH adjuster of component (F) is used to adjust the pH to be 6 or less.

The cosmetic of the present invention preferably has a low alkali metal ion concentration to inhibit the hydrolysis of component (A) in the cosmetic.

The form of the cosmetic of the present invention is not particularly limited, and any form such as a skin lotion, a lotion, a milky lotion, a serum, a cream, a mask, an ointment, a dispersion, a solid matter, and a mousse can be used.

EXAMPLES

<Measurement Method>
1. pH Measurement
10% by mass aqueous solution of a sample was used to measure at 25° C.
2. Viscosity Measurement
B-type viscometer (rotor No. 4, 6 rpm) was used to measure at 25° C.
3. Measurement of Residual Rate (%) of L-Ascorbyl Tetra Fatty Acid Ester (Component A)
Measurement was made by using a sample immediately after preparation and a sample stored at 40° C. for 6 months. The sample was weighed at a specified amount, a mobile phase was added thereto for uniform dissolution, and then, the resulting mixture was filtered through a 0.45 μm filter for liquid chromatograph to obtain a sample solution. Additionally, VC-IP standard was dissolved in a mobile phase to give a standard solution. 20 μL of each of the sample solution and the standard solution were quantitatively determined by liquid chromatography under the following conditions.

VC-IP residual rate (%)=(VC-IP quantitative value in the sample stored at 40° C. for 6 months/VC-IP quantitative value in the sample immediately after preparation)×100

(Chromatography Conditions)
Column temperature: 30° C.
Mobile phase: ethanol:methanol:chloroform (volume ratio: 4:4:2)
Measurement wavelength: ultraviolet absorbance (wavelength of 240 nm)
Flow rate: 1.0 mL/min
Column: ODS (4.6 mmϕ×150 nm)
4. Component Used (All Manufactured by Nikko Chemicals Co., Ltd)
NIKKOL VC-IP: ascorbyl tetrahexyldecanoate
NIKKOL CIO: cetyl ethylhexanoate (an IOB value of 0.128)
NIKKOL Trifat S-308: triethylhexanoin (an IOB value of 0.353)
NIKKOL Triester F-810: caprylic/capric triglyceride (an IOB value of 0.274)
NIKKOL Batyl Alcohol EX: batyl alcohol
NIKKOL Behenyl Alcohol 65: behenyl alcohol
NIKKOL SS-10V: sorbitan stearate
NIKKOL N-SPV: cetyl palmitate
NIKKOL MGS-150V: glyceryl stearate, PEG-60 glyceryl stearate
NIKKOL Hexaglyn PR-15: polyglyceryl-6 polyricinoleate
NIKKOL Sugarsqualane: squalane
NIKKOL Jojoba Oil S: jojoba oil
NIKKOL Nikkomulese LH: glycerin, hydrogenated lecithin, hydroxypropyl methylcellulose stearoxy ether, squalane, sodium methyl stearoyl taurate
NIKKOL Trifat PS-45H: hydrogenated palm oil, Elaeis guineensis (palm) kernel oil, Elaeis guineensis (palm) oil
NIKKOL Lecinol S-10: hydrogenated lecithin Example 1 (Examples 1-1 and 1-2)

pH Evaluation

Each of the first phase and the second phase shown in Table 1 is weighed and heated to dissolve uniformly. Subsequently, the first phase was gradually added to the second phase and the mixture was emulsified with homogenizer. Then, the mixture was cooled to 40° C. and the third phase was added to the mixture to obtain a cosmetic. Each numerical value of respective components in the Table represents % by mass.

TABLE 1

|  | Example 1-1 | Example 1-2 |
|---|---|---|
| <First phase component> | | |
| NIKKOL Sugarsqualane | 10.00 | 10.00 |
| (B) NIKKOL Trifet S-308 | 10.00 | 10.00 |
| (G) Stearyl alcohol | 3.50 | 3.50 |
| (A) NIKKOL VC-IP | 3.00 | 3.00 |
| NIKKOL Nikkomulese 41 | 2.50 | 2.50 |
| NIKKOL MGS-BV2 | 2.00 | 2.00 |
| NIKKOL Batyl Alcohol 100 | 0.50 | 0.50 |
| (D) Antioxidant | q.s. | q.s. |
| Preservative | q.s. | q.s. |
| <Second phase component> | | |
| Xanthan gum (2% aq.) | 10.00 | 10.00 |
| Glycerin | 10.00 | 10.00 |
| 1,3-Butylene glycol | 5.00 | 5.00 |
| NIKKOL Lecinol S-10 | 0.20 | 0.20 |
| (C) Chelating agent | q.s. | q.s. |
| (E) Water | Balance | Balance |
| <(F) pH adjuster> | | |
| Citric acid (1% aq.) | 2.00 | 1.00 |
| Trisodium citrate (1% aq.) | 3.00 | 4.00 |
| Water | 5.00 | 5.00 |
| Total amount (% by mass) | 100.00 | 100.00 |
| <Stability test evaluation> | | |
| Initial value pH | pH 4.8 | pH 5.8 |
| VC-IP content (%) in preparation | 2.95 | 2.94 |
| 40° C./6M VC-IP content (%) in preparation | 2.46 | 2.32 |
| VC-IP residual rate (%) | 83.39 | 78.91 |

The polar oil of component (B), the chelating agent of component (C), and the antioxidant of component (D) were used and the pH was adjusted, and as a result, the hydrolysis of component (A) was inhibited. With a pH of 6 or less, the hydrolysis of component (A) was more inhibited in Example 1-1 in which the cosmetic had a lower pH of 5.5 or less.

Example 2 (Examples 2-1, 2-2)

Buffer Evaluation

The respective components shown in Table 2 were used to prepare cosmetics in the same way as in Example 1.

TABLE 2

|  | Example 2-1 | Example 2-2 |
|---|---|---|
| <First phase component> | | |
| NIKKOL Sugarsqualane | 10.00 | 10.00 |
| (B) NIKKOL Trifat S-308 | 10.00 | 10.00 |
| (G) Stearyl alcohol | 3.50 | 3.50 |
| (A) NIKKOL VC-IP | 3.00 | 3.00 |
| NIKKOL Nikkomulese 41 | 2.50 | 2.50 |
| NIKKOL MGS-BV2 | 2.00 | 2.00 |
| NIKKOL Batyl Alcohol 100 | 0.50 | 0.50 |
| (D) Antioxidant | q.s. | q.s. |
| Preservative | q.s. | q.s. |
| <Second phase component> | | |
| Xanthan gum (2% aq.) | 10.00 | 10.00 |
| Glycerin | 10.00 | 10.00 |
| 1,3-Butylene glycol | 5.00 | 5.00 |
| NIKKOL Lecinol S-10 | 0.20 | 0.20 |
| (C) Chelating agent | q.s. | q.s. |
| (E) Water | Balance | Balance |
| <(F) pH adjuster, buffer> | | |
| Citric acid (1% aq.) | 2.00 | |
| Trisodium citrate (1% aq.) | 3.00 | |
| Succinic acid (1% aq.) | | 4.00 |
| NaOH (1% aq.) | | 1.00 |
| Water | 5.00 | 5.00 |
| Total amount (% by mass) | 100.00 | 100.00 |
| <Stability test evaluation> | | |
| Initial value pH | 5.590 | 5.412 |
| Viscosity (mPa · s) | 59200 | 62100 |
| VC-IP content (%) in preparation | 2.96 | 2.93 |
| 40° C. · 6M VC-IP content (%) in preparation | 2.26 | 2.31 |
| VC-IP residual rate (%) | 76.35 | 78.84 |

The polar oil of component (B), the chelating agent of component (C), the antioxidant of component (D), and the higher alcohol of component (G) (3.50% by mass) were used and the pH was adjusted, and as a result, the hydrolysis of component (A) was inhibited. With a pH of 6 or less, the hydrolysis of component (A) was more inhibited in Example 2-2 in which the cosmetic had a lower pH of 5.5 or less. Additionally, the use of succinic acid having a chelating effect as a pH adjuster in Example 2-2 seems to have affected the inhibition of the hydrolysis of component (A).

Example 3 (Examples 3-1, 3-2, and 3-3)

Chelating Agent Evaluation

The respective components shown in Table 3 were used to prepare cosmetics in the same way as in Example 1.

TABLE 3

|  | Example 3-1 | Example 3-2 | Example 3-3 |
|---|---|---|---|
| <First phase component> | | | |
| NIKKOL Sugarsqualane | 10.00 | 10.00 | 10.00 |
| (B) NIKKOL Trifat S-308 | 10.00 | 10.00 | 10.00 |
| (G) Stearyl alcohol | 3.50 | 3.50 | 3.50 |
| (A) NIKKOL VC-IP | 3.00 | 3.00 | 3.00 |
| NIKKOL Nikkomulese 41 | 2.50 | 2.50 | 2.50 |
| NIKKOL MGS-BV2 | 2.00 | 2.00 | 2.00 |
| NIKKOL Batyl Alcohol 100 | 0.50 | 0.50 | 0.50 |
| (D) Antioxidant | q.s. | q.s. | q.s. |
| Preservative | q.s. | q.s. | q.s. |
| <Second phase component> | | | |
| Xanthan gum (2% aq.) | 10.00 | 10.00 | 10.00 |
| Glycerin | 10.00 | 10.00 | 10.00 |
| 1,3-Butylene glycol | 5.00 | 5.00 | 5.00 |
| NIKKOL Lecinol S-10 | 0.20 | 0.20 | 0.20 |
| (C) Chelating agent (EDTA) | 0.05 | | |
| (C) Chelating agent (EDTA-2Na) | | 0.05 | |
| (C) Chelating agent (succinic acid) | | | 0.05 |
| (E) Water | Balance | Balance | Balance |
| (F) pH adjuster | q.s. | q.s. | q.s. |
|  | 100.00 | 100.00 | 100.00 |
| <Stability test evaluation> | | | |
| Initial value pH | 5.37 | 5.59 | 5.18 |
| Viscosity (mPa · s) | 12300 | 59200 | 11700 |
| VC-IP content (%) in preparation | 2.92 | 2.96 | 2.89 |
| 40° C./6M VC-IP content (%) in preparation | 2.36 | 2.26 | 2.35 |
| VC-IP residual rate (%) | 80.82 | 76.35 | 81.31 |

The polar oil of component (B), the chelating agent of component (C), the antioxidant of component (D), and a small amount of component (G) (3.50% by mass) were used and the pH was adjusted, and as a result, the hydrolysis of component (A) was inhibited. The inhibitory effect on the hydrolysis of component (A) by the chelating agent of component (C) was higher in the order of succinic acid (Example 3-3), EDTA (Example 3-1), EDTA-2Na (Example 3-2), and the presence of Na ion seems to have caused a decrease in inhibitory effect in Example 3-2.

Example 4 (Examples 4-1 and 4-2) and Comparative Example 1

Polar Oil Evaluation (EO-Based Formulation)

Each of the first phase and the second phase shown in Table 4 is weighed and warmed to dissolve uniformly. Subsequently, the first phase was gradually added to the second phase and the mixture was emulsified with a homogenizer. Then, the mixture was cooled to 40° C. to obtain a cosmetic.

TABLE 4

|  | Comparative Example 1 | Example 4-1 | Example 4-2 |
|---|---|---|---|
| <First phase component> | | | |
| NIKKOL Sugarsqualane | 20.00 | 10.00 | 0.00 |
| (B) NIKKOL Trifat S-308 | — | 10.00 | 20.00 |
| (G) Cetyl alcohol | 5.00 | 5.00 | 5.00 |
| (A) NIKKOL VC-IP | 3.00 | 3.00 | 3.00 |
| NIKKOL BB-20 | 2.00 | 2.00 | 2.00 |
| NIKKOL MGS-BV2 | 1.00 | 1.00 | 1.00 |

TABLE 4-continued

|  | Comparative Example 1 | Example 4-1 | Example 4-2 |
|---|---|---|---|
| (D) Antioxidant | q.s. | q.s. | q.s. |
| Preservative | q.s. | q.s. | q.s. |
| <Second phase component> | | | |
| Xanthan gum (2% aq.) | 5.00 | 5.00 | 5.00 |
| 1,3-Butylene glycol | 5.00 | 5.00 | 5.00 |
| (C) Chelating agent | q.s. | q.s. | q.s. |
| (F) pH adjuster | q.s. | q.s. | q.s. |
| (E) Water | Balance | Balance | Balance |
| Total amount (% by mass) | 100.00 | 100.00 | 100.00 |
| <Stability test evaluation> | | | |
| Initial value pH | 3.923 | 3.76 | 3.862 |
| Viscosity (mPa·s) | 40900 | 31200 | 47700 |
| VC-IP content (%) in preparation | 2.88 | 2.92 | 2.88 |
| 40° C.·6M VC-IP content (%) in preparation | 0.98 | 2.45 | 2.67 |
| VC-IP residual rate (%) | 35.13 | 86.27 | 92.71 |

The description "—" indicates no addition.

In Examples 4-1 and 4-2, the polar oil of component (B), the chelating agent of component (C), the antioxidant of component (D), and a small amount of component (G) (5.00% by mass) were used and the pH was adjusted, and as a result, the hydrolysis of component (A) was inhibited. Without component (B), a poorer inhibitory effect on the hydrolysis of component (A) was shown in Comparative Example 1. The inhibitory effect on the hydrolysis of component (A) was higher in Example 4-2 than that in Example 4-1. This is because the compatibility with component (A) was: the polar oil of component (B)>nonpolar oil (squalane), and the combination of the polar oil of component (B) and component (A) having good compatibility with each other seems to have prevented component (A) from transferring into water.

Example 5 (Examples 5-1 and 5-2) and Comparative Example 2

Polar Oil Evaluation (Anion-Based Formulation)

The respective components shown in Table 5 were used to prepare cosmetics in the same way as in Example 1.

TABLE 5

|  | Comparative Example 2 | Example 5-1 | Example 5-2 |
|---|---|---|---|
| <First phase component> | | | |
| NIKKOL Sugarsqualane | 20.00 | 10.00 | — |
| (B) NIKKOL Trifat S-308 | — | 10.00 | 20.00 |
| (G) Stearyl alcohol | 3.50 | 3.50 | 3.50 |
| (A) NIKKOL VC-IP | 3.00 | 3.00 | 3.00 |
| NIKKOL Nikkomulese 41 | 2.50 | 2.50 | 2.50 |
| NIKKOL MGS-BV2 | 2.00 | 2.00 | 2.00 |
| NIKKOL Batyl Alcohol 100 | 0.50 | 0.50 | 0.50 |
| (D) Antioxidant | q.s. | q.s. | q.s. |
| Preservative | q.s. | q.s. | q.s. |
| <Second phase component> | | | |
| Xanthan gum (2% aq.) | 10.00 | 10.00 | 10.00 |
| Glycerin | 10.00 | 10.00 | 10.00 |
| 1,3-Butylene glycol | 5.00 | 5.00 | 5.00 |

TABLE 5-continued

|  | Comparative Example 2 | Example 5-1 | Example 5-2 |
|---|---|---|---|
| NIKKOL Lecinol S-10 | 0.20 | 0.20 | 0.20 |
| (C) Chelating agent | q.s. | q.s. | q.s. |
| (E) Water | Balance | Balance | Balance |
| (F) pH adjuster | q.s. | q.s. | q.s. |
| Total amount (% by mass) | 100.00 | 100.00 | 100.00 |
| <Stability test evaluation> | | | |
| Initial value pH | 5.541 | 5.59 | 5.747 |
| Viscosity (mPa·s) | 30100 | 59200 | 60200 |
| VC-IP content (%) in preparation | 2.89 | 2.96 | 2.92 |
| 40° C./6M VC-IP content (%) in preparation | 1.53 | 2.26 | 2.49 |
| VC-IP residual rate (%) | 52.94 | 76.35 | 85.27 |

The description "—" indicates no addition.

In Examples 5-1 and 5-2, the polar oil of component (B), the chelating agent of component (C), the antioxidant of component (D), and a small amount of component (G) (3.50% by mass) were used and the pH was adjusted, and as a result, the hydrolysis of component (A) was inhibited. Without component (B), a poorer inhibitory effect on the hydrolysis of component (A) was shown in Comparative Example 2. Comparing Example 5-1 with Example 5-2, the inhibitory effect on the hydrolysis of component (A) was higher in Example 5-2 in which the proportion of the polar oil of component (B) was higher. This is because the compatibility with component (A) was: the polar oil of component (B)>nonpolar oil (squalane), and the combination of the polar oil of component (B) and component (A) having good compatibility with each other seems to have prevented component (A) from transferring into water.

Example 6 (Examples 6-1, 6-2, and 6-3)

Higher Alcohol Evaluation

The respective components shown in Table 6 were used to prepare cosmetics in the same way as in Example 1.

TABLE 6

|  | Example 6-1 | Example 6-2 | Example 6-3 |
|---|---|---|---|
| <First phase component> | | | |
| NIKKOL Sugarsqualane | 10.00 | 10.00 | 10.00 |
| (B) NIKKOL Trifat S-308 | 10.00 | 10.00 | 10.00 |
| (A) NIKKOL VC-IP | 3.00 | 3.00 | 3.00 |
| NIKKOL MGS-BV2 | 2.00 | 2.00 | 2.00 |
| NIKKOL Deca.5-SV | 0.95 | 0.95 | 0.95 |
| NIKKOL Batyl Alcohol 100 | 0.50 | 0.50 | 0.50 |
| Sodium stearoyl lactylate 12% | 0.30 | 0.30 | 0.30 |
| (G) Behenyl alcohol | 4.75 | — | — |
| (G) Stearyl alcohol | — | 4.75 | — |
| (G) Cetyl alcohol | — | — | 4.75 |
| (D) Antioxidant | q.s. | q.s. | q.s. |
| Preservative | q.s. | q.s. | q.s. |
| <Second phase component> | | | |
| Xanthan gum (2% aq.) | 10.00 | 10.00 | 10.00 |
| Glycerin | 10.00 | 10.00 | 10.00 |
| 1,3-Butylene glycol | 5.00 | 5.00 | 5.00 |
| NIKKOL Lecinol S-10 (L.4818) | 0.20 | 0.20 | 0.20 |

TABLE 6-continued

|  |  | Example 6-1 | Example 6-2 | Example 6-3 |
|---|---|---|---|---|
| (C) Chelating agent |  | q.s. | q.s. | q.s. |
| (E) Water |  | Balance | Balance | Balance |
| (F) pH adjuster |  | q.s. | q.s. | q.s. |
| Total amount (% by mass) |  | 100.00 | 100.00 | 100.00 |
| <Stability test evaluation> |  |  |  |  |
| Initial value | pH | 4.462 | 4.494 | 4.331 |
|  | Viscosity (mPa · s) | 6000 | 15300 | 41200 |
|  | VC-IP content (%) in preparation | 2.89 | 2.92 | 3.13 |
| 40° C./6M | VC-IP content (%) in preparation | 2.59 | 2.45 | 2.48 |
| VC-IP residual rate (%) |  | 89.62 | 83.90 | 79.23 |

The description "—"indicates no addition.

In Example 6-1, 6-2, and 6-3, the polar oil of component (B), the chelating agent of component (C), the antioxidant of component (D), and a small amount of component (G) (4.75% by mass) were used and the pH was adjusted, and as a result, the hydrolysis of component (A) was inhibited. When the alcohol of component (G) was used, the alcohol having more carbons exhibited a higher inhibitory effect on the hydrolysis of component (A). This is because the higher alcohol is present on the interface between the first phase (oil phase) and the second phase (aqueous phase), and the alcohol having more carbons seems to make component (A) in the first phase (oil phase) hard to transfer to the second phase (aqueous phase).

Example 7 (Examples 7-1, 7-2, and 7-3)

Evaluation of Amount Blended of Higher Alcohol

The respective components shown in Table 7 were used to prepare cosmetics in the same way as in Example 1.

TABLE 7

|  | Example 7-1 | Example 7-2 | Example 7-3 |
|---|---|---|---|
| <First phase component> |  |  |  |
| NIKKOL Sugarsqualane | 10.00 | 10.00 | 10.00 |
| (B) NIKKOL Trifat S-308 | 10.00 | 10.00 | 10.00 |
| (A) NIKKOL VC-IP | 3.00 | 3.00 | 3.00 |
| (G) Stearyl alcohol | 2.50 | 4.75 | 7.00 |
| NIKKOL MGS-BV2 | 2.00 | 2.00 | 2.00 |
| NIKKOL Deca.5-SV | 0.95 | 0.95 | 0.95 |
| NIKKOL Batyl Alcohol 100 | 0.50 | 0.50 | 0.50 |
| Sodium stearoyl lactylate 12% | 0.30 | 0.30 | 0.30 |
| (D) Antioxidant | q.s. | q.s. | q.s. |
| Preservative | q.s. | q.s. | q.s. |
| <Second phase component> |  |  |  |
| Xanthan gum (2% aq.) | 10.00 | 10.00 | 10.00 |
| Glycerin | 10.00 | 10.00 | 10.00 |
| 1,3-Butylene glycol | 5.00 | 5.00 | 5.00 |
| NIKKOL Lecinol S-10 | 0.20 | 0.20 | 0.20 |
| (C) Chelating agent | q.s. | q.s. | q.s. |
| (E) Water | Balance | Balance | Balance |
| (F) pH adjuster | q.s. | q.s. | q.s. |
| Total amount (% by mass) | 100.00 | 100.00 | 100.00 |
| <Stability test evaluation> |  |  |  |
| Initial value  pH | 4.338 | 4.494 | 4.505 |
| Viscosity (mPa · s) | 9300 | 15300 | 34000 |
| VC-IP content (%) in preparation | 2.95 | 2.92 | 2.90 |

TABLE 7-continued

|  |  | Example 7-1 | Example 7-2 | Example 7-3 |
|---|---|---|---|---|
| 40° C./6M | VC-IP content (%) in preparation | 2.69 | 2.45 | 2.29 |
| VC-IP residual rate (%) |  | 91.19 | 83.90 | 78.97 |

In Examples 7-1, 7-2, and 7-3, the polar oil of component (B), the chelating agent of component (C), the antioxidant of component (D), and component (G) were used and the pH was adjusted, and as a result, the hydrolysis of component (A) was inhibited. When the higher alcohol of component (G) was used, a lower amount of component (G) increased the inhibitory effect on the hydrolysis of component (A). A larger amount of component (G) increases the amount of component (G) dissolved in the first phase (oil phase), and this causes the hydroxyl group of component (G) to react with component (A), which results in the decrease in the inhibitory effect on the hydrolysis of component (A).

Example 8

Milky Lotion

| First phase | NIKKOL SS-10V | 0.5 |
|---|---|---|
|  | NIKKOL N-SPV | 0.5 |
|  | NIKKOL Batyl Alcohol EX | 0.2 |
|  | NIKKOL VC-IP | 3.0 |
|  | NIKKOL Sugarsqualane | 2.0 |
|  | NIKKOL CIO | 6.0 |
|  | NIKKOL Jojoba Oil S | 1.0 |
|  | KF-96A-6cs (dimethicone) | 2.0 |
|  | KF-995 (cyclomethicone) | 4.0 |
|  | Tocopherol | 0.2 |
| Second phase | NIKKOL Nikkomulese LH | 3.0 |
|  | Xanthan gum (2% aqueous solution) | 10.0 |
|  | 1,3-Butylene glycol | 4.0 |
|  | Glycerin | 5.0 |
|  | Disodium edetate | 0.1 |
|  | Succinic acid (1% aqueous solution) | 4.0 |
|  | Sodium hydroxide (1% aqueous solution) | 1.0 |
|  | Preservative | q.s. |
|  | Water | balance |
| (Total) |  | 100.0% by mass |

Preparation method: each of the first phase and the second phase was heated to 80° C. The first phase was gradually added to the second phase and the mixture was emulsified with a homogenizer. After emulsifying, the mixture was cooled to the room temperature and corrected for water to obtain a milky lotion.

Results: the pH immediately after preparation was 4.484 (10% aqueous solution), and the viscosity was 10300 (B-type viscometer, rotor No. 4, 6 rpm). The VC-IP residual rate after storage at 40° C. for 6 months was 90% or more.

Example 9

Cream

| First phase | NIKKOL Triester F-810 | 4.0 |
|---|---|---|
|  | NIKKOL VC-IP | 3.0 |
|  | NIKKOL Trifat PS-45H | 4.0 |
|  | NIKKOL Behenyl Alcohol 65 | 2.0 |

|        |                                      |      |
|--------|--------------------------------------|------|
|        | NIKKOL Batyl Alcohol EX              | 1.0  |
|        | NIKKOL N-SPV                         | 3.0  |
|        | NIKKOL MGS-150V                      | 2.0  |
|        | KF-96A-100cs (dimethicone)           | 0.2  |
|        | NIKKOL Lecinol S-10                  | 0.1  |
|        | Tocopherol                           | 0.1  |
|        | Preservative                         | q.s. |
| Second | Hydroxyethylcellulose                | 2.0  |
| phase  | Xanthan gum (2% aqueous solution)    | 2.0  |
|        | 1,3-Butylene glycol                  | 5.0  |
|        | Glycerin                             | 3.0  |
|        | Citric acid (1% aqueous solution)    | 2.0  |
|        | Sodium citrate (1% aqueous solution) | 3.0  |
|        | Edetic acid                          | 0.1  |
|        | Water                                | balance |
|        | (Total)                              | 100.0% by mass |

Preparation method: a cream was obtained in the same way as in Example 8.

Results: the pH immediately after preparation was 5.214 (10% aqueous solution), and the viscosity was 27000 (B-type viscometer, rotor No. 4, 6 rpm). The VC-IP residual rate after storage at 40° C. for 6 months was 90% or more.

Example 10

Serum

|        |                                                     |         |
|--------|-----------------------------------------------------|---------|
| First  | Glycerin                                            | 2.0     |
| phase  | 1,3-Butylene glycol                                 | 2.0     |
|        | Pentylene Glycol                                    | 3.0     |
|        | Dipropylene Glycol                                  | 3.0     |
|        | Xanthan gum (2% aqueous solution)                   | 1.0     |
|        | Acrylates/Alkyl Methacrylate Copolymer (2% aqueous solution) | 15.0 |
|        | EDTA-2Na                                            | 0.05    |
| Second | L-arginine (10% aqueous solution)                   | 1.0     |
| phase  | Water                                               | balance |
| Third  | NIKKOL Trifat S-308                                 | 3.0     |
| phase  | NIKKOL VC-IP                                        | 3.0     |
|        | KF-54 (methyl phenyl silicone)                      | 1.0     |
|        | NIKKOL Hexaglyn PR-15                               | 1.0     |
|        | Tocopherol                                          | 0.1     |
|        | Preservative                                        | q.s.    |
|        | (Total)                                             | 100.0% by mass |

Preparation method: the first phase was made uniform by stirring with a paddle mixer, and when it became uniform, the second phase was added thereto. When the mixture became further uniform, the third phase was added thereto and the mixture was stirred sufficiently to obtain a serum.

Results: the pH immediately after preparation was 5.174 (10% aqueous solution), and the viscosity was 3100 (B-type viscometer, rotor No. 4, 6 rpm). The VC-IP residual rate after storage at 40° C. for 6 months was 90% or more.

Example 11

Gel Cream

|       |                                   |      |
|-------|-----------------------------------|------|
| First | Glycerin                          | 4.0  |
| phase | 1,3-Butylene glycol               | 6.0  |
|       | Preservative                      | q.s. |
|       | Xanthan gum (2% aqueous solution) | 4.0  |
|       | Carboxy vinyl polymer (2% aqueous solution) | 33.0 |
|       | Pentasodium pentetate             | 0.10 |
| Second | L-arginine                       | 0.1  |
| phase | Water                             | balance |
| Third | NIKKOL VC-IP                      | 30.0 |
| phase | NIKKOL Triester F-810             | 5.0  |
|       | NIKKOL Hexaglyn PR-15             | 0.5  |
|       | Tocopherol                        | 0.3  |
|       | (Total)                           | 100.0% by mass |

Preparation method: the first phase was made uniform by stirring with a paddle mixer, and when it became uniform, the second phase was added thereto. When the mixture became further uniform, the third phase was added thereto and the mixture was stirred sufficiently to obtain a gel cream.

Results: the pH immediately after preparation was 4.65 (10% aqueous solution), and the viscosity was 88,000 (B-type viscometer, rotor No. 4, 6 rpm). The VC-IP residual rate after storage at 40° C. for 6 months was 90% or more.

INDUSTRIAL APPLICABILITY

The cosmetic of the present invention can be utilized as basic cosmetic products and makeup cosmetic products.

The invention claimed is:

1. An oil-in-water emulsion cosmetic comprising the following (A) to (E) as essential components and having a pH of 6 or less:
   (A) an L-ascorbyl tetra fatty acid ester derivative represented by the following general formula (I)

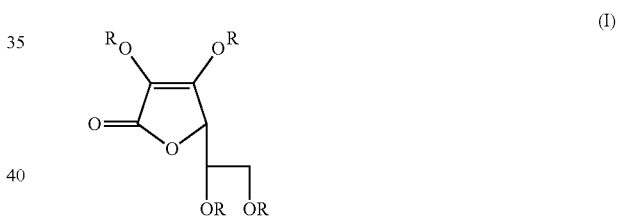

wherein R represents a branched alkyl fatty acid residue having 8 to 18 carbons;
   (B) a caprylic/capric triglyceride polar oil, the caprylic/capric triglyceride polar oil being a liquid at 25° C. and having an IOB value of 0.1 to 0.5;
   (C) a chelating agent;
   (D) an antioxidant; and
   (E) water,
wherein (A) and (B) are compatible with each other and when combined inhibit hydrolysis of (A).

2. The oil-in-water emulsion cosmetic according to claim 1, wherein the component (C) chelating agent is one or two or more selected from edetic acid and a salt thereof, succinic acid and a salt thereof, and pentetic acid and a salt thereof.

3. The oil-in-water emulsion cosmetic according to claim 1, further comprising one or two or more selected from citric acid and a salt thereof, succinic acid and a salt thereof, phosphoric acid and a salt thereof, sodium hydroxide, and potassium hydroxide, as a component (F) pH adjuster.

4. The oil-in-water emulsion cosmetic according to claim 1, further comprising, in the cosmetic, 8% by mass or less of a component (G) higher alcohol having 16 or more carbons.

* * * * *